US007276997B2

United States Patent
Lvovsky et al.

(10) Patent No.: US 7,276,997 B2
(45) Date of Patent: Oct. 2, 2007

(54) APPARATUS FOR POSITIONING A NON-IMAGED EXTREMITY DURING A MAGNETIC IMAGING PROCESS

(75) Inventors: Yuri Lvovsky, Florence, SC (US); Rory John Warner, Oxford (GB)

(73) Assignee: General Electric, Schenectady, NY (US)

( * ) Notice: Subject to any disclaimer, the term of this patent is extended or adjusted under 35 U.S.C. 154(b) by 295 days.

(21) Appl. No.: 11/046,414

(22) Filed: Jan. 29, 2005

(65) Prior Publication Data

US 2006/0181382 A1    Aug. 17, 2006

(51) Int. Cl.
*H01F 5/00*    (2006.01)
(52) U.S. Cl. ........................ 335/299; 335/296
(58) Field of Classification Search ........ 335/296–299, 335/216
See application file for complete search history.

(56) References Cited

U.S. PATENT DOCUMENTS

| | | | |
|---|---|---|---|
| 4,608,991 A | | 9/1986 | Rollwitz |
| 5,646,532 A | | 7/1997 | Knuttel et al. |
| 5,659,281 A | * | 8/1997 | Pissanetzky et al. ........ 335/296 |
| 5,678,549 A | | 10/1997 | Heywang-Koebrunner et al. |
| 6,288,624 B1 | * | 9/2001 | Savelainen .................. 335/299 |
| 6,567,683 B1 | * | 5/2003 | Knuettel ..................... 600/410 |
| 2004/0030241 A1 | | 2/2004 | Green et al. |
| 2006/0055406 A1 | * | 3/2006 | Lvovsky et al. ............ 324/318 |
| 2006/0173278 A1 | * | 8/2006 | Wahl et al. ................. 600/410 |
| 2006/0261813 A1 | * | 11/2006 | Schuster et al. ............ 324/318 |
| 2007/0063801 A1 | * | 3/2007 | Laskaris .................... 335/301 |

FOREIGN PATENT DOCUMENTS

| | | |
|---|---|---|
| GB | 2417562 A | 3/2006 |
| JP | 9140684 A | 11/1995 |

\* cited by examiner

*Primary Examiner*—Elvin Enad
*Assistant Examiner*—Bernard Rojas
(74) *Attorney, Agent, or Firm*—Peter Vogel; William Baxter; Ellis B. Ramirez

(57) ABSTRACT

An apparatus for magnetic resonance imaging having a magnetic assembly with a main magnet, a shielding system positioned outside the main magnet, and a first and second space for positioning the imaged and non-imaged extremity. Various apparatus with distinct vessels and casings are described with a magnetic assembly and ferromagnetic shielding systems. In yet a further aspect, an apparatus for resonance imaging having additional shim elements for compensating effects from non-axisymmetrical shape of ferromagnetic shielding casing is disclosed. Additionally, an apparatus for magnetic resonance imaging is described having a dedicated space outside the imaging region and where the dedicated space has support element for resting non-image extremity as part of the structure of the imager.

6 Claims, 7 Drawing Sheets

APPARATUS FOR POSITIONING A NON-IMAGED EXTREMITY DURING A MAGNETIC IMAGING PROCESS

FIELD OF THE INVENTION

This invention relates generally to magnetic resonance imaging (MRI) apparatus. More particularly, this invention relates to an MRI apparatus having a region for a non-imaged extremity.

BACKGROUND OF THE INVENTION

MRI scanners, which are used in various fields such as medical diagnostics, typically use a computer to create images based on the operation of a magnet, a gradient coil assembly, and a radiofrequency coil(s). The magnet creates a uniform main magnetic field, which makes nuclei, such as that of hydrogen atoms, responsive to radiofrequency excitation. The gradient coil assembly imposes a series of pulsed, spatially varying magnetic fields upon the main magnetic field, in order to give each point in the imaging volume a spatial identity corresponding to its unique magnetic field values during the imaging pulse sequence. The radiofrequency coil(s) generate(s) an excitation frequency pulse that causes a temporary oscillating transverse magnetization of the nuclei. The nuclei relaxation from that states results in an emitted signal which is detected by the radiofrequency coil and used by the computer to create the image.

The typical MRI system is provided with shielding means designed to prevent exposure to static stray magnetic field to the operator, surrounding equipment and facilities. The typical stray magnetic field limit imposed by the U.S. Food and Drug Administration (FDA) with respect to external personnel exposure is 5 gauss; additional stray field limitations of higher values may be imposed in the design to prevent interference with electronics and other nearby equipment.

The shielding means of superconductive magnets may include superconductive bucking coils (active shielding) and/or ferromagnetic (iron) shielding elements. The superconductive bucking coils carry electric currents of generally opposite direction to the electric current carried in the superconductive main coils. The superconductive bucking coils are positioned radially outward from the superconductive main coils to counterbalance magnetic moments created by the main coils. Likewise, the cylindrical iron shield is positioned radially outward from the superconductive main coils to prevent leakage outside the magnet of the magnetic field created by the main coils.

Orthopedics is a medical specialty concerned with correction of deformities or functional impairments of the skeletal system, particularly, of the extremities and the spine, and associated structures, such as muscles and ligaments. For example, diagnosis and treatment of broken hand or leg bones is a common practice in orthopedics. Because many orthopedic health problems are subcutaneous, imaging anatomy under the skin is a very important capability in orthopedics. Magnetic resonance imaging (MRI) is one imaging technique implemented in orthopedic diagnosis.

Use of conventional whole body (WB) MRI systems in orthopedic imaging has its intrinsic limitations. The distance between the front face and the field of view is hardly sufficient to allow the patient to extend their arm or leg into the centrally located field of view from the outside of the MRI system, therefore patients must egress into the center of the MRI even for orthopedic imaging of limbs. For claustrophobic patients, this can be a traumatic experience. In addition, the large size and large stray field footprint of conventional WB MRI systems require a large floor space in which to site the MRI system and associated increased facilities cost. Furthermore, conventional full body MRI systems have higher cost than the dedicated orthopedic system, as the large bore inevitably leads to much larger overall dimensions, forces and amount of superconductor, as well as complexity of structural and cryogenic designs.

Thus, in the case of orthopedic application for MRI systems there are considerable advantages in terms over cost and sitability for small diameter bore magnet systems dedicated to extremity imaging such as human legs and arms. However, an orthopedic MRI system suffers from the limitation that the shielding increases the outside dimensions of the magnet system which limits the access for leg imaging due to the difficulty of positioning the subject's second leg outside the imaging region.

For the reasons stated above, and for other reasons stated below which will become apparent to those skilled in the art upon reading and understanding the present specification, there is a need in the art for orthopedic imaging that is not limited by the outside dimensions of the magnet system. There is also a need for improved magnetic resonance imaging of extremities, which does not compromise or affect the accuracy or operation of the MRI.

BRIEF DESCRIPTION OF THE INVENTION

The above-mentioned shortcomings, disadvantages and problems are addressed herein, which will be understood by reading and studying the following specification.

SUMMARY OF THE INVENTION

An apparatus for resonance imaging having a magnetic assembly positioned about the center of a vessel comprising main coils and/or other means to generate main magnetic field, e.g. ferromagnetic elements, having an inner diameter and an outer diameter for magnetic resonance imaging, and regions between the main magnetic assembly and a shielding system so as to position the imaging extremity in the center and non-imaging extremity in the region between the main magnetic assembly and the shield system.

In yet another aspect, an apparatus for resonance imaging having a main magnetic assembly positioned about the center of an annulus vessel comprising a main coil assembly and/or other means to generate main magnetic field, e.g. ferromagnetic elements, having an inner diameter and an outer diameter, a gradient system adjacent to the magnetic assembly, shielding assembly, and regions between the gradient assembly and magnetic assembly so as to position the non-imaging extremities.

An magnetic resonance imaging system is described having a magnetic assembly positioned in an annulus vessel, a ferromagnetic shielding casing positioned around the magnetic assembly and in partial contact with the magnetic assembly, a first space for placing the imaged extremity in the bore of said magnetic assembly, a second space adjacent to said portion of said ferromagnetic casing which is in contact with said magnetic assembly for positioning the non-imaged extremity, and additional shim elements for compensating effects from non-axisymmetrical shape of said ferromagnetic shielding casing.

In a further aspect, an apparatus for resonance imaging having a magnetic assembly positioned about the center of a vessel comprising a main coil assembly and/or other means to generate main magnetic field, e.g. ferromagnetic elements, having an inner diameter and an outer diameter, a shielding assembly and shim elements for placement within the magnetic assembly so as to become magnetized and compensate magnetic field inhomogeneities created by non-axisymmetric shape of shielding assembly elements, and regions in the annulus vessel to position the non-imaging extremities.

In yet a further aspect, an apparatus for resonance imaging having a magnetic assembly positioned about the center of an annulus vessel comprising a main coil assembly and/or other means to generate main magnetic field, e.g. ferromagnetic elements, having an inner diameter and an outer diameter, a shim elements for placement within the magnetic assembly so as to become magnetized and compensate magnetic field inhomogeneities created by non-axisymmetric shape of shielding assembly elements, and a substantially bulge shape region and a annular shape region between the shield and main magnetic assembly to position the non-imaging extremity.

In still yet a further aspect, an apparatus for resonance imaging having a magnetic assembly positioned about the center of a warped annulus vessel resembling a clover leaf shape comprising a main coil assembly and/or other means to generate main magnetic field, e.g. ferromagnetic elements, having an inner diameter and an outer diameter. The lobes of the cloverleaf vessel is used to position the non-imaging extremities In addition to the aspects and advantages described in this summary, further aspects and advantages will become apparent by reference to the drawings and by reading the detailed description that follows.

DETAILED DESCRIPTION OF THE INVENTION

In the following detailed description, reference is made to the accompanying drawings that form a part hereof, and in which is shown by way of illustration specific embodiments which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
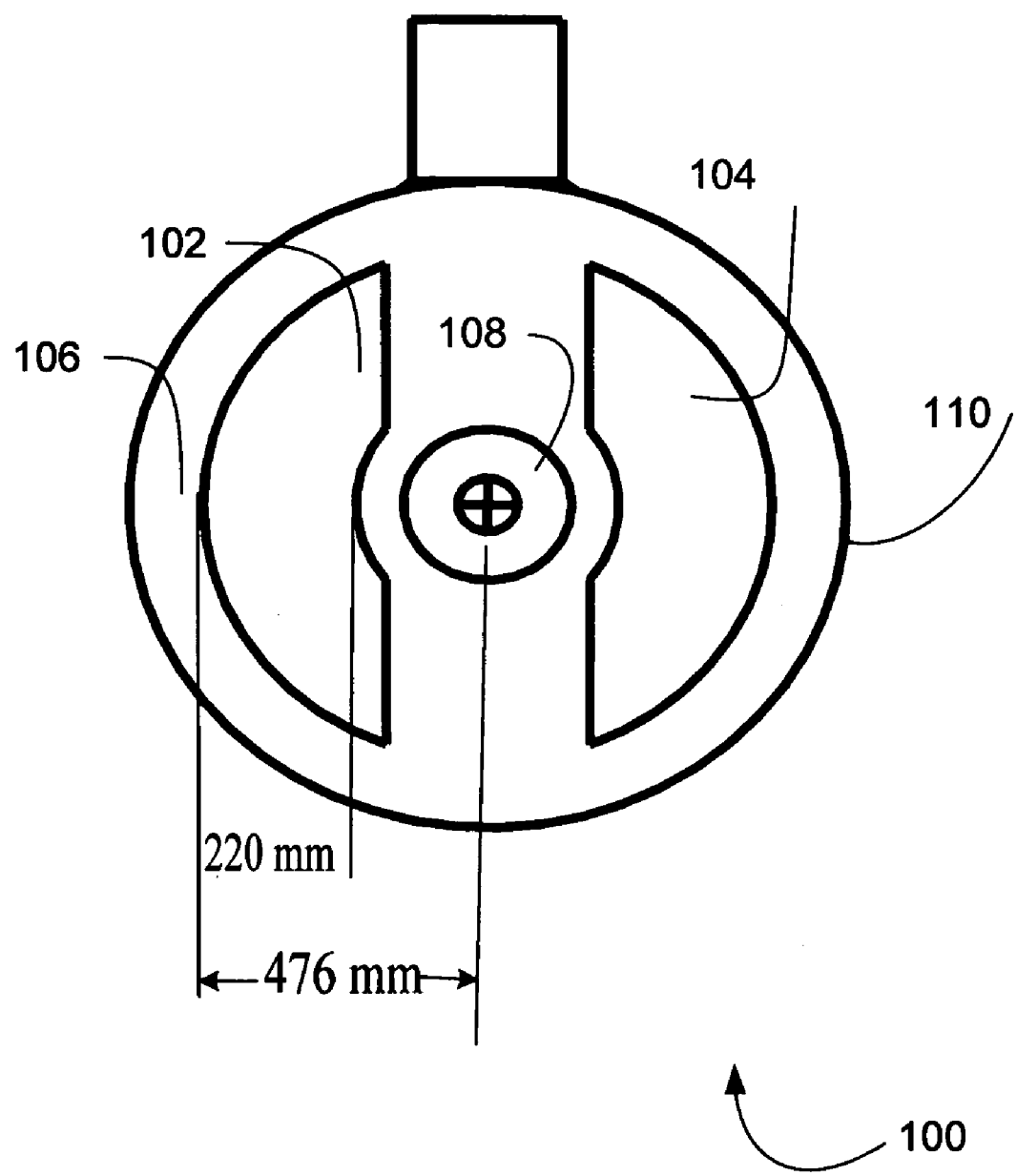
FIG. 1 is an end view of a vessel according to an embodiment for positioning extremities for medical resonance imaging.

FIG. 1 is an end view that provides a system level overview of an apparatus having an annulus outer perimeter to image a subject using magnetic resonance. It should be understood, however, that the underlying concepts are not depended upon a particular shape so it is conceivable that other shapes can be used without departing from the inventive concepts. System 100 solves the need in the art for more comfortable access to an MRI system by a patient during imaging of an extremity of the patient. System 100 also solves the need in the art for reduced floor space requirements of MRI systems.

System 100 includes a casing 110 having an annular shaped outer perimeter while a leg or arm of the patient is placed in the system 100 for imaging. The imaged extremity is placed in the bore of the magnet 108 and the non-imaged extremity is placed in either space 102 or 104. Thus, system 100 solves the need in the art for more comfortable access to a MRI system by a patient during imaging of an extremity's of the patient. In addition, the small overall outer diameter 208 of the casing 110 reduces floor space requirement of the MRI system. The smaller length does not require egress into the center of the entire system for orthopedic medical imaging, which more readily accommodates claustrophobic patients.

System 100 also includes a first annular space 102 and second annular space 104 in the annulus casing 110. The magnet for imaging has a magnetic assembly or plurality of magnetic coils (not shown) positioned in the casing 110 around the bore in close proximity to the first annular space 102 and the second annular space 104. When imaging of an extremity is being performed the patient will insert it in the bore and use either space 102 or 104 to rest the non-imaging extremity. Further, positioned inside the outer edge of annulus vessel 110 is a shielding system 106. The shielding system 106 can include active shielding such as superconductive bucking coil, or passive ferromagnetic shielding, or any known or future developed shielding. In the latter implementation, the shielding system 106 can be a room temperature shielding such as iron or like that surrounds the main magnetic assembly and substantially reduces leakage stray field so as to protect space outside of the annulus casing. When the MRI system is being used, for example for imaging legs, the non-imaged extremity can be placed in either annular space 102 or 104. Otherwise, the non-imaged extremity would extend outside the annulus casing 110 causing discomfort to the patient and limiting the region that can be imaged.

Figure 2:
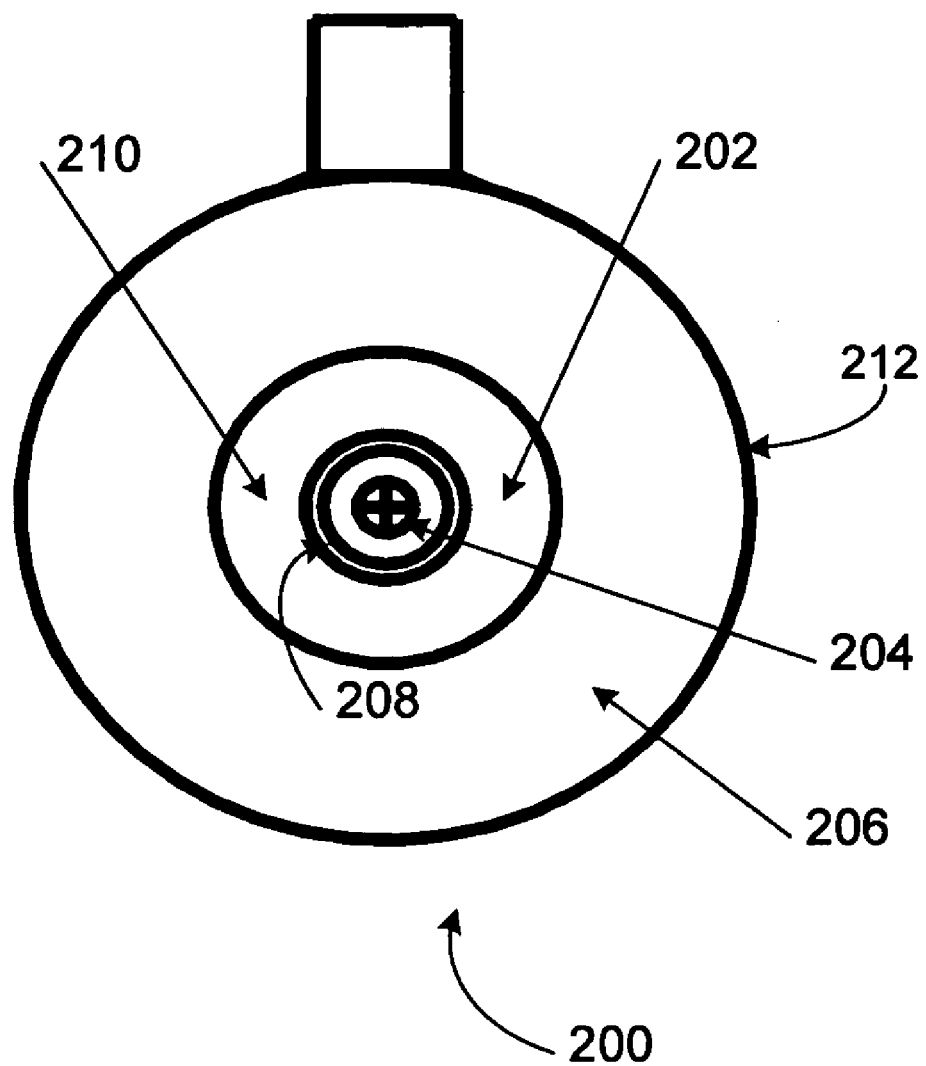
FIG. 2 is an end view of a vessel according to an embodiment for positioning extremities for medical resonance imaging between a gradient system and magnetic system.

FIG. 2 is an end view that provides a system level overview of an apparatus having an annulus outer perimeter 212 to image a subject using magnetic resonance. System 200 solves the need in the art for more comfortable access to an MRI system by a patient during imaging of an extremity. System 200 also solves the need in the art for reduced floor space requirements of MRI systems by encasing the system the MRI in a casing with smaller outer diameter The smaller size does not require egress into the center of the entire system for orthopedic medical imaging, which more readily accommodates claustrophobic patients.

System 200 also includes a first area 202 and a second area 210 within the annulus casing 212 for positioning a non-imaged extremity. A magnetic assembly creates a Field of View (FOV) 204 in the bore of casing 212 in close proximity to the first area 202 and the second area 210. The imaged extremity is then placed in the bore to be imaged by the MRI system 200 while the non-imaged extremity can be comfortably placed in either area 202 or 210. The coils or other magnetic field generated devices can be placed in space 206 along with the necessary shielding for the MRI system 200 which is positioned closer to the outer edge 212 of the annulus vessel. Additionally, a gradient structure 208 can be positioned adjacent to the FOV 204 or in the alternative the gradient structure 208 could be placed adjacent to the magnetic field generating devices in space 206. In the later arrangement the first and second areas 202 and 210 are between the gradient system 208 and the top part of the bore. The shielding in space 206 can be active shielding such as superconductive bucking coil, passive ferromagnetic shielding, or any known or future developed shielding that can be placed inside or on outside an annulus vessel. When the MRI system is being used for imaging legs, the non-imaged leg can be placed in either area 202 or 210. Otherwise, the non-imaged leg would extend outside the annulus casing 212 causing discomfort to the patient and limiting the region that can be imaged.

Figure 3:
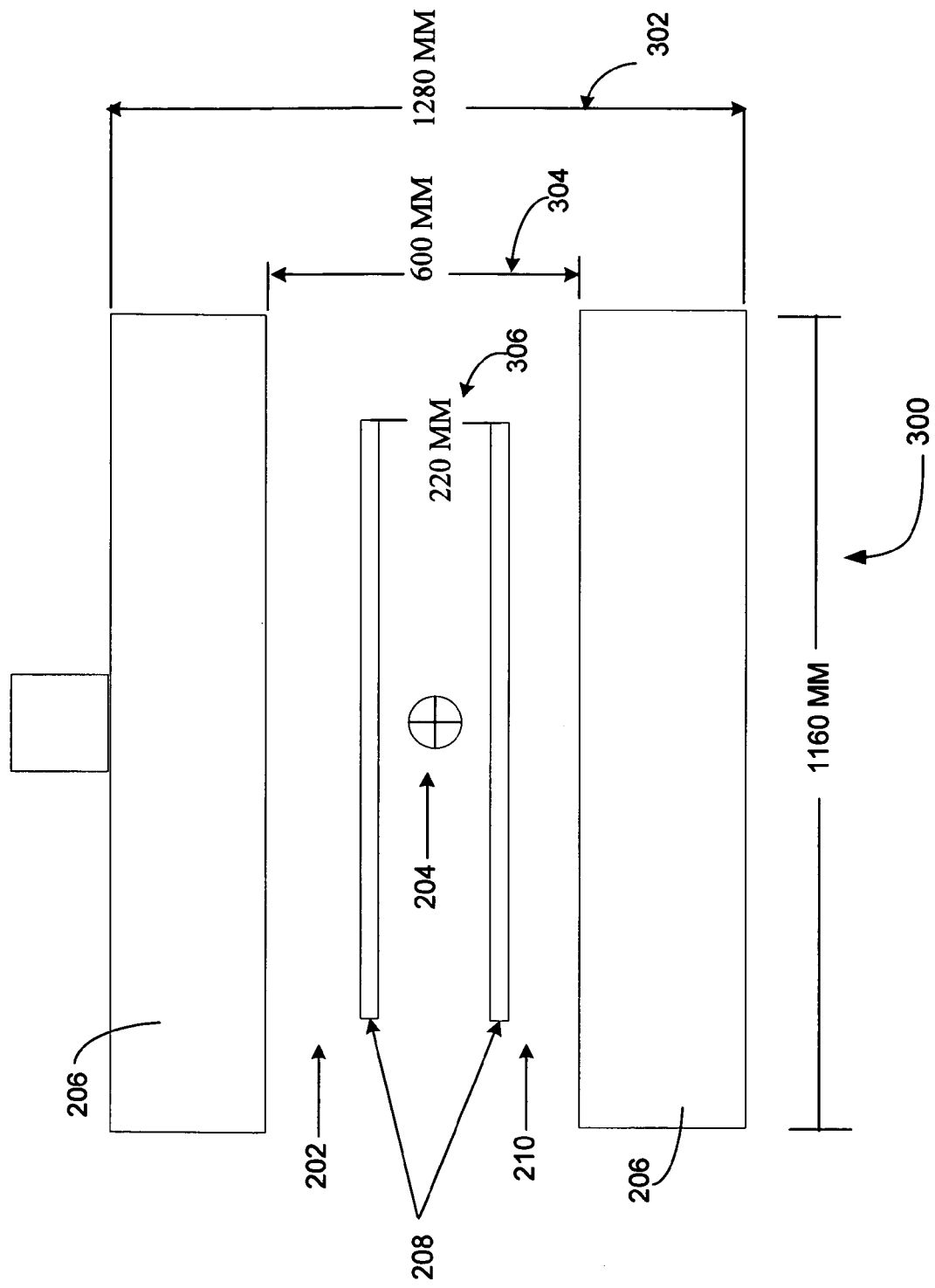
FIG. 3 is a side view (vertical cross-section) of the MRI system according to an embodiment.

FIG. 3 is a side view diagram that provides an apparatus having an annulus outer perimeter to image a subject using magnetic resonance. System 300 includes the entrance to the bore 306 for positioning the imaged extremity at the imaging region 204 so as to perform imaging of extremities, gradient structure, and entry points or first and second areas 202,210 for positioning the non-imaged extremity. Furthermore, 302 shows the diameter of the casing, 306 shows the dimension for the entrance to the bore, and 304 shows the diameter of the combined first and second areas and the entrance to the bore. Those in the art should understand that these dimensions are only for illustration purposes and that these dimensions could be changed or altered without departing from the spirit of the invention.

Figure 4:
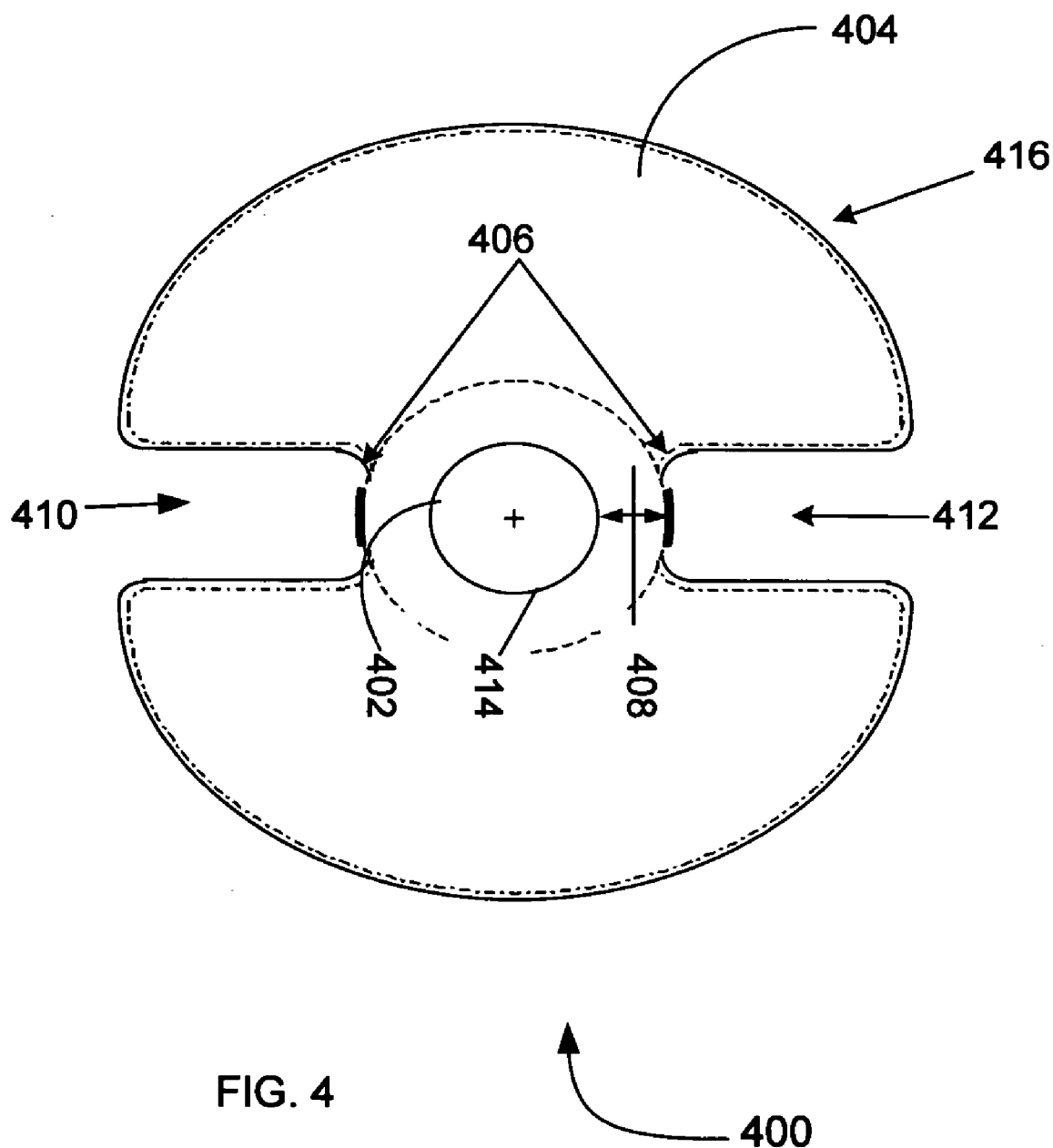
FIG. 4 is an end view of an annulus vessel according to an embodiment for positioning extremities for medical resonance by the use of cut outs.

FIG. 4 is an end view that provides a system level overview of an apparatus having an annulus outer perimeter to image a subject using magnetic resonance. MRI System 400 solves the need in the art for more comfortable access to an MRI system by a patient during imaging of an extremity of the patient. System 400 also solves the need in the art for reduced floor space requirements of MRI systems.

The MRI System 400 includes a first space 410 and second space 412 that have been cutout from an otherwise circular casing 416. The shielding system 416 is a ferromagnetic envelope. In the alternative, the casing 416 can be defined as a region that ends at spaces 410 and 412 and takes the shape as shown in FIG. 4. A magnetic assembly and shielding system (not shown) can be positioned in the casing 416 in region 404 in close proximity to bore 402 where a field of view (FOV) is created for imaging an extremity. When the MRI system is being used for imaging legs the non-imaged leg can be placed in either annular space 410 or 412 that have been cutout from annulus casing 416. Otherwise, the non-imaged leg would extend outside the casing 416 causing discomfort to the patient and limiting the region that can be imaged. When annular spaces 410 or 412 are cutout from the annulus vessel 416 the possibility that the shielding in 404 is not substantial to isolate stray magnetic field from outside the vessel is increased. To circumvent non-uniform contribution to the imaging field caused by such leakage, shimming elements 406 can be placed substantially near the outer diameter (OD) 414 of bore 402. These additional shimming elements compensate from non-axisymmetrical shape of said ferromagnetic shielding casing The shimming elements 406 are selected based on a process known as shimming to improve the homogeneity of the magnetic field produced by magnetic assembly to the necessary levels by making small adjustments to the overall magnetic field. In the case of passive shimming, the shim elements 406 are placed within the magnetic field so as to become magnetized and have an effect on the magnetic field. A non-magnetic holder receives the shim element such that the shim element is disposed at a fixed position with respect to the magnet. In the alternative, the shim elements could be placed in either a dedicated mounting or welded on the surface of the magnet. The shim element 406 may represent a plurality of shim elements of the same or varying sizes. The magnetic material may be a soft ferromagnetic material. radial terms can be attenuated by proper positioning accomplished through iterative measuring and calibration or magnetic analysis that can be used to determine the proper shim elements 406.

Figure 5:
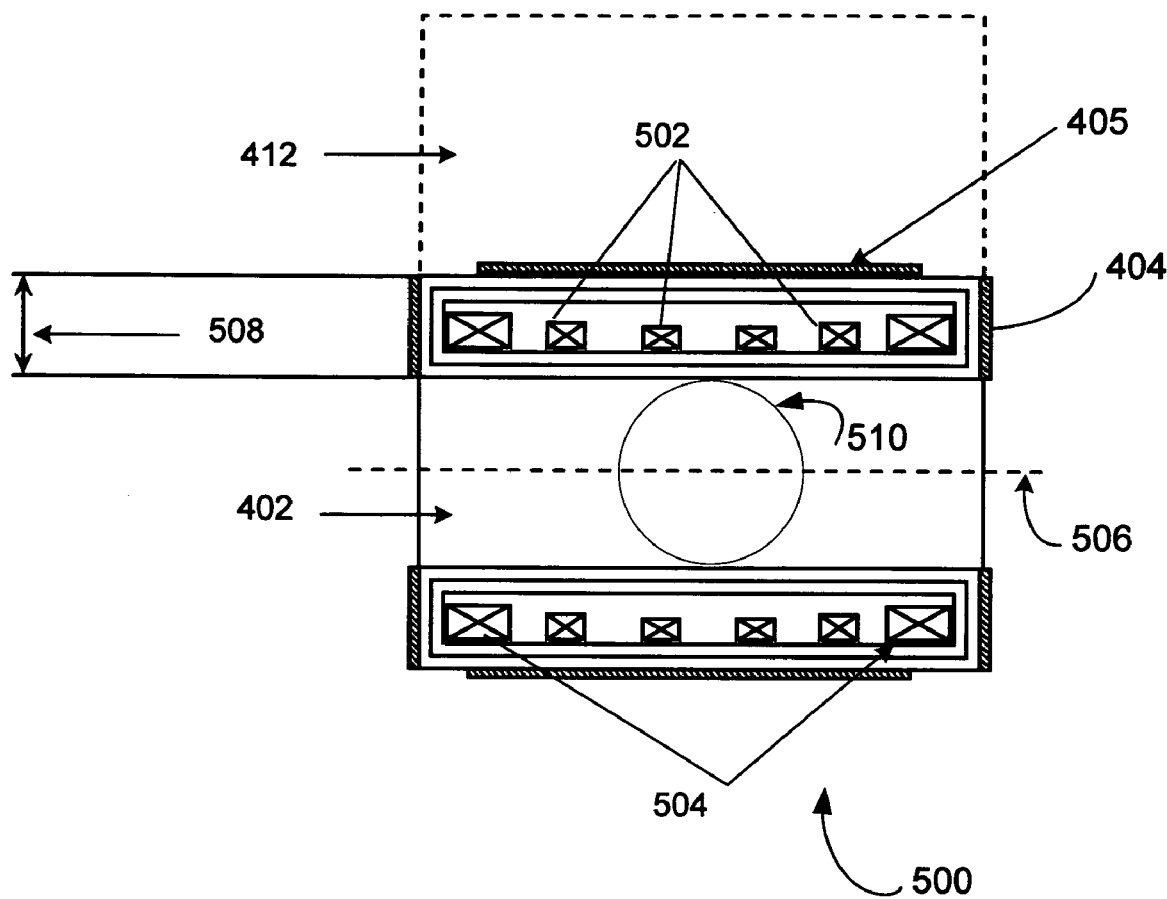
FIG. 5 is a top view (horizontal cross-section) of the MRI system according to an embodiment.

FIG. 5 is a horizontal cross-sectional view that provides a system level overview of an apparatus having an outer perimeter to image a subject using magnetic resonance. System 500 solves the need in the art for more comfortable access to an MRI system by a patient during imaging of an extremity of the patient. System 500 also solves the need in the art for reduced floor space requirements of MRI systems.

System 500 shows a second space 412 and view of the inner part of the bore 402 where the imaging of extremities is conducted along path 506. Further, part of the magnetic system such as field shaping coils 502 that with end coils 504 produce a magnetic field for imaging of extremities are shown at field of view 510. The distance between imaged and non-imaged leg is represented by 508.

Figure 6:
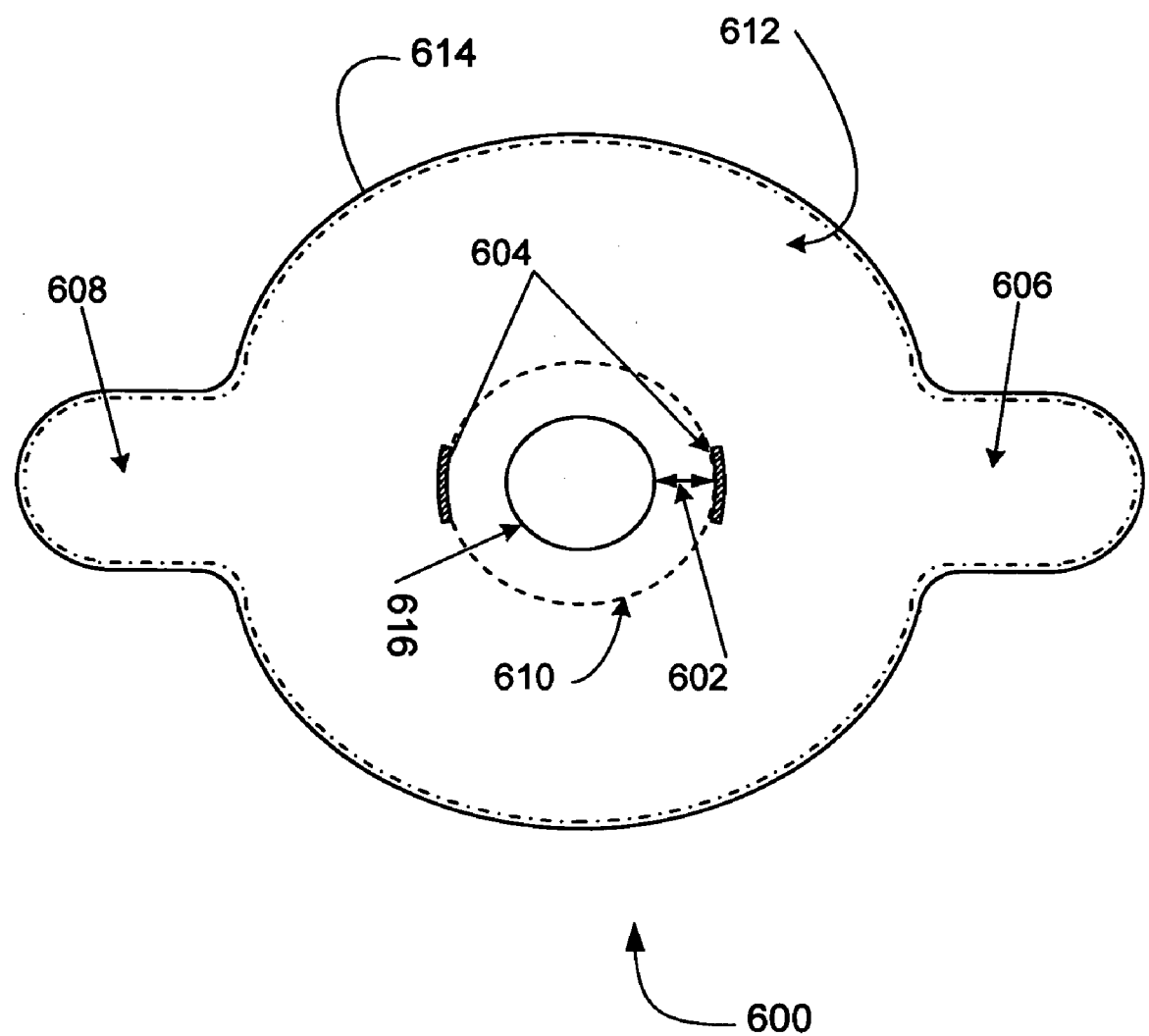
FIG. 6 is an end view of an annulus vessel according to an embodiment for positioning extremities for medical resonance by the use of bulges in the shielding system.

FIG. 6 is an end view that provides a system level overview of an apparatus having an annulus outer perimeter to image a subject using magnetic resonance. System 600 solves the need in the art for more comfortable access to an MRI system by a patient during imaging of an extremity of the patient. System 600 also solves the need in the art for reduced floor space requirements of MRI systems.

System 600 includes a casing 614 capable of holding imaged and non-imaged extremities, magnetic assembly, and shielding system. System 600 also includes a first space 606 and second space 608 in the annulus casing 614. These spaces are for positioning the non-imaged extremity during the imaging cycle. For example, if imaging at field of view (FOV) 616 the right leg or arm a patient (facing system 600) could rest the non-imaged extremity in space 608. A magnetic assembly or pluralities of magnetic coils (not shown) are positioned in the casing 614 in close proximity to the first annular space 606 and the second annular space 608. The MRI system 600 may use ferromagnetic shielding (not shown) which may be at room temperature (RT) and may form part of the outer casing at 612 for example, or be part of the imaging room. RT shielding on outside the magnet use less space then the actively-shielded magnet with bucking coils, and provides the opportunity for accommodating second, non-imaged leg or arm.

To avoid effect of changing magnetization with ambient temperature, the temperature of the RT shield may be automatically controlled by maintaining it constant, and elevated over that of the room e.g. by using heaters. In embodiments where RT shielding is used, an asymmetric magnet exerts a non-zero axial force on the symmetric RT shielding thus affecting internal suspension system, thus the RT shield is formed asymmetric to achieve balanced zero axial force. System 600 shows additional shim elements 604 that are positioned at a predetermined distance from field of view 616 at the outer edge of the bore 610. The additional shim elements become magnetized and have an effect of the projected magnetic field produced by the magnetic system.

Figure 7:
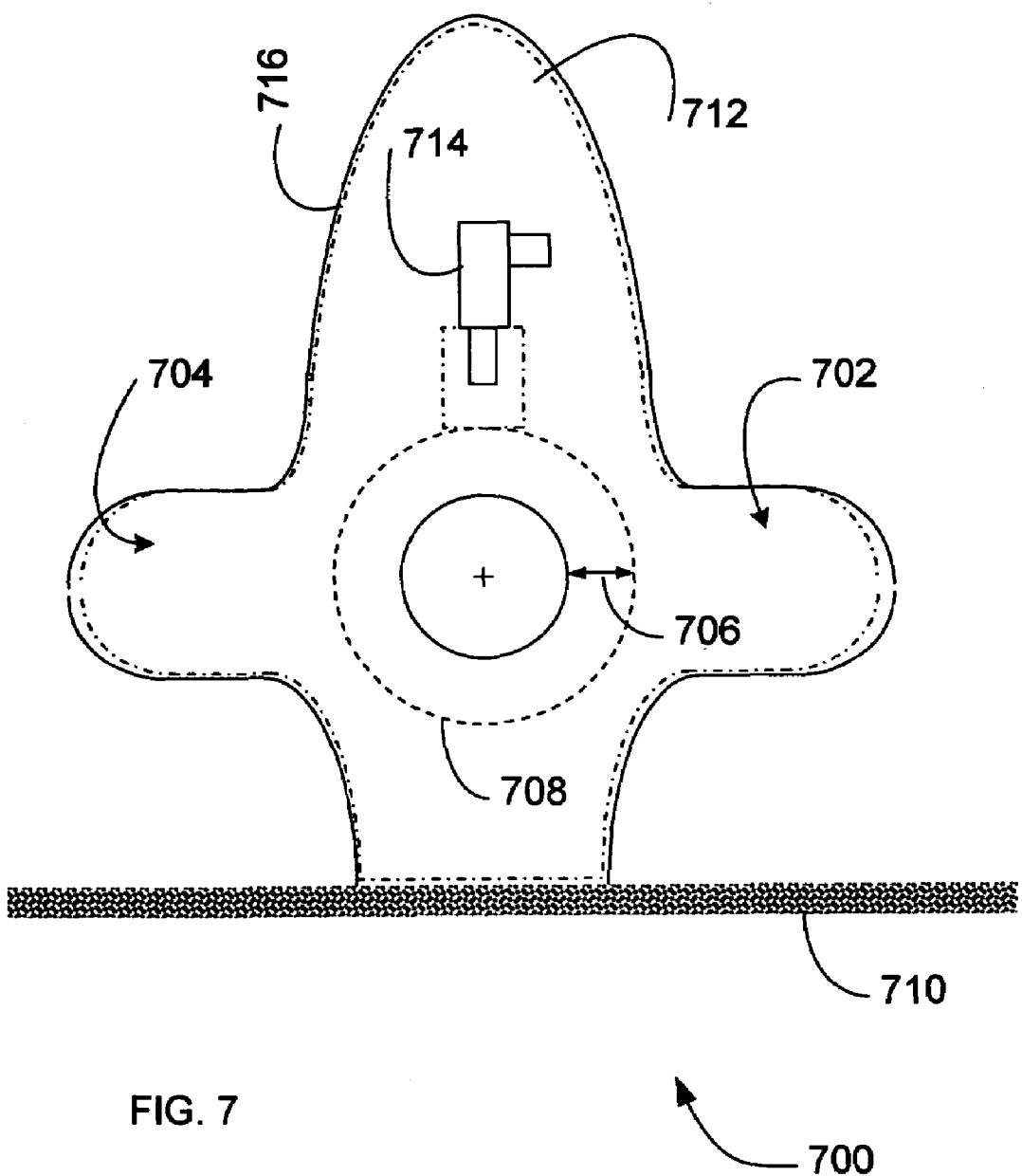
FIG. 7 is an end view of an annulus vessel according to an embodiment for positioning extremities for medical resonance imaging in a clover-type shape.

FIG. 7 is an end view that provides a system level overview of an apparatus to image a subject's extremities using magnetic resonance. In FIG. 7, system 700 solves the need in the art for more comfortable access to an MRI system by a patient during imaging of an extremity of the patient. System 700 also solves the need in the art for reduced floor space requirements of MRI systems. The casing resembles the shape of a cloverleaf that is anchor on floor 710. As shown in FIG. 7 first and second spaces 702, 704 are bulges protruding or distorting an otherwise ring like shape of the vessel.

System 700 includes a casing 716 in a cloverleaf-type shaped system. The magnet 708 is built in the conventional manner and the distance 706 from the field of view (FOV) is the same as the previously described implementations. The casing has been stretched at different parts leading to the bulges and resembling a cloverleaf with a cutoff bottom for placing on floor 710. System 700 shows non-axisymmetric shielding a space for positioning a non-imaged extremity. The smaller length of the dedicated orthopedic imager does not require egress into the center of the entire system for orthopedic medical imaging, which more readily accommodates claustrophobic patients. System 700 also includes a first space 702 and second space 704 in the casing 716. The regions 702 and 704 are farther positioned from the magnetic assembly resulting in an air gap between the magnet and the non-imaged extremity. A magnetic assembly (not shown) is positioned in close proximity to the first annular space 702 and the second annular space 704 in the inner part of the casing such as in space 712. The casing 716 acts as a shielding system when a non-axisymmetric ferromagnetic envelope is fashioned into part of the cloverleaf shape. One positive effect of this non-axisymmetric shielding is that magnetic field is mostly confined to the fourth order radial terms. When the MRI system 700 is being used for imaging legs the non-imaged leg can be placed in either space 702 or 704. Otherwise, the non-imaged leg would extend outside the casing 716 causing discomfort to the patient and limiting the region that can be imaged. Further, within the casing 716 a space can be provided for service area such as electrical supplies, cryocooler, and storage for other needed supplies.

CONCLUSION

A MRI system has been described. Although specific embodiments have been illustrated and described herein, it will be appreciated by those of ordinary skill in the art that any arrangement which is calculated to achieve the same purpose may be substituted for the specific embodiments shown. This application is intended to cover any adaptations or variations. For example, although described as using an annulus vessel, one of ordinary skill in the art will appreciate that implementations can be made in any shape or any size that provides the required function.

We claim:

1. An apparatus for magnetic resonance imaging, the apparatus positioned being inside a vessel, the apparatus comprising:
    a magnetic assembly comprising a main magnetic assembly comprising magnetic field generating elements, the magnetic field generating elements having an inner diameter and an outer diameter for imaging an extremity;
    a shielding system positioned outside the main magnetic assembly; a first space between said magnetic assembly and said shielding system; and
    a second space between said magnetic assembly and said shielding system;
    wherein a non-imaged extremity may be placed in the first or second space;
    wherein the shielding system further comprises bucking coils.

2. The apparatus of claim 1, wherein the shielding system further comprises:
    an outer vacuum casing and ferromagnetic shielding elements provided as part outer casing or a separate element attached to said vessel.

3. The apparatus of claim 1, wherein the vessel further comprises a cryostat.

4. An apparatus for magnetic resonance imaging, the apparatus comprising:
    a magnetic assembly for creating an imaging field region for magnetic resonance imaging of extremities; and,
    a dedicated space outside the imaging region for positioning a non-imaged extremity;
    wherein the dedicated space further comprises support element for resting non-image extremity as part of the structure of the imager.

5. The apparatus of claim 4, further comprising:
    a central bore within said magnetic assembly; and
    wherein the dedicated space is outside the bore.

6. The apparatus of claim 5, wherein said dedicated space runs parallel to said central bore.

* * * * *